United States Patent [19]

Gough et al.

[11] Patent Number: 5,523,080

[45] Date of Patent: Jun. 4, 1996

[54] COSMETIC TREATMENT OF SUBSTRATES

[75] Inventors: Anthony D. Gough, Swansea; Ezat Khoshdel, Merseyside; Robert Polywka, Chester, all of Great Britain

[73] Assignee: Chesebrough-Pond's USA Co., Division of Conopco, Inc., Greenwich, Conn.

[21] Appl. No.: 245,110

[22] Filed: May 17, 1994

[30] Foreign Application Priority Data

May 18, 1993 [GB] United Kingdom ............ 9310241

[51] Int. Cl.⁶ .................................................. A61K 7/06
[52] U.S. Cl. .................. 424/70.12; 424/70.15; 424/78.36; 424/78.38
[58] Field of Search .............. 424/70.1, 70.12, 424/78.03, 78.36, 70.15; 526/260, 279; 132/202

[56] References Cited

U.S. PATENT DOCUMENTS

| Re. 34,958 | 5/1995 | Garbe et al. | 424/70.12 |
|---|---|---|---|
| 3,577,517 | 5/1991 | Kubot et al. | 424/47 |
| 3,583,950 | 6/1991 | Kollinsky et al. | 525/326.8 |
| 4,097,444 | 6/1978 | Teige et al. . | |
| 4,543,249 | 9/1985 | Nelson | 424/70.16 |
| 4,556,554 | 12/1985 | Calvo | 4/844 |
| 4,867,966 | 9/1989 | Grollier et al. | 424/70.12 |
| 4,981,933 | 1/1991 | Faxio et al. . | |
| 5,013,795 | 5/1991 | Coleman et al. . | |
| 5,021,477 | 6/1991 | Garbe et al. | 424/70.12 |
| 5,166,276 | 11/1992 | Hayama et al. | 525/329.7 |
| 5,200,471 | 4/1993 | Coleman et al. . | |
| 5,292,514 | 3/1994 | Capecchi et al. | 424/422 |
| 5,344,701 | 9/1994 | Gagnon et al. | 428/304.4 |

FOREIGN PATENT DOCUMENTS

| 0392735 | 10/1990 | European Pat. Off. . |
|---|---|---|
| 1121418 | 7/1968 | United Kingdom . |
| 1202119 | 8/1970 | United Kingdom . |
| 1558847 | 1/1980 | United Kingdom . |

*Primary Examiner*—Melvyn I. Marquis
*Assistant Examiner*—Robert H. Harrison
*Attorney, Agent, or Firm*—Milton L. Honig

[57] ABSTRACT

A method for treating hair to impart thereto a conditioning benefit, the method involving applying to the hair an azlactone-functionalised copolymer consisting of vinyl azlactone and methacryloyl polydimethylsiloxane monomers; and allowing the copolymer to chemically bond through nucleophilic reaction of the azlactone onto the hair, the monomers of the copolymer being present in amounts sufficient to achieve both bonding to the hair and imparting conditioning properties.

2 Claims, No Drawings

COSMETIC TREATMENT OF SUBSTRATES

BACKGROUND OF THE INVENTION

1. Field of the Invention

This invention relates to compositions and methods for the cosmetic treatment of substrates, particularly the surface of materials in the form of fibres or essentially flat structures. More particularly, the invention relates to the cosmetic treatment of substrates which, owing to the chemical nature of the material, present at their surface at least one species of nucleophilic group for chemical interaction with one or more cosmetic substances with which the material surface is to be treated. Such substrates include for example proteinaceous materials such as keratin, e.g., as found in hair, skin and nails and various animal body parts such as horns, hooves and feathers, and other naturally occurring protein containing materials, e.g., silk and saccharide-derived materials such as those derived from cellulose or cellulose derivatives e.g. natural products such as cotton. The invention is concerned particularly with the treatment of these kinds of substrates with substances which impart one or more tactile, visual or other cosmetic benefits.

2. The Related Art

It is well known and well documented in the relevant technical and patent literature that fibrous materials such as hair and fabrics or the like can be treated with cosmetic agents which deliver one or more desirable cosmetic benefits, for example, conditioning, setting or styling. Such treatment extends not only to fibrous materials, but also to materials which are substantially flat, like skin. Conventionally these treatments are carried out by applying to the surface of the material usually a composition containing the one or more active ingredients which serve to impart the benefit or benefits which are wanted.

The application of such conventional cosmetic treatment compositions to achieve the desired results relies essentially on two key factors: firstly, it is important that the active ingredient or ingredients with which the substrate is to be treated are provided in a form of composition which on the one hand is stable upon storage and maintains the essential treatment agent or agents in cosmetically active form, and on the other hand allows the active(s) to be deposited from the composition onto the substrate surface, which deposition imparts the desired benefit to a sufficient degree and in an economical manner; secondly, it is essential that once deposited the cosmetic active or actives are retained on the substrate surface, so that when the treatment is completed and for example the substrate is rinsed to remove unwanted excess composition or residual components thereof, sufficient of the cosmetic active substance or substances remains bonded to the substrate surface so as to impart the intended characteristic cosmetic benefit or benefits thereto.

This bonding of active material to the treated substrate surface is generally of the nature of physisorption; that is to say, molecules of the cosmetic active(s) are absorbed onto the surface of the substrate by virtue of physical intermolecular forces such as hydrogen bonding. Conventionally, it has been accepted that this form of retention of active substances on treated substrate surfaces gives adequate results as regards achievable cosmetic benefits and economics, and this is perhaps an explanation of why efforts over recent years have been towards improving the technology of deposition itself as a means for improving the efficacy and economy of cosmetic products.

A major problem, however, associated with known cosmetic products, even those which employ advanced patented deposition systems, is that once a substrate has been treated with a cosmetic agent, because of the very nature of the physical forces which bond the active to the substrate material, retention of the cosmetic agent at the desired site of application is frequently short-lived. Most frequently, this temporary retention is brought about by the need for washing of for example the skin, hair, other fibres or other substrates which have been treated with the cosmetic active. Often particular cosmetic actives are applied to a substrate material in the first place during or immediately following a washing treatment, and so unless such cosmetic treatment is repeated at the time of each wash, any kind of performance or retention for a period in excess of a period between washes is difficult to achieve. Admittedly, over recent years there have been moves to use cosmetic treatment compositions and regimes which are milder and less harsh to hair, other fibres or skin or the like, but even so the act itself of washing to remove dirt and excess oils and so on generally also removes any valuable cosmetic agent which is wanted for retention to impart a particular benefit with some long lasting effect.

Not only does the above problem mean that the efforts in the art towards advanced deposition systems represent at best a partial solution to an overall underlying problem, but it also demonstrates the significant shortcomings of conventional cosmetic product technology with regard to inefficient, uneconomical use and waste of cosmetic raw materials. With recent public awareness leaning towards avoidance of environmental contaminants and possible risks to the health of animals and plants, a reduction in the amount of synthetic, frequently non-naturally degradable materials transported into the environment following use by human consumers would also be a welcome advance.

As relevant prior art to the present invention there may be mentioned EP-A-0392735 (Minnesota Mining and Manufacturing Company), which discloses certain azlactone-functional polymeric solid supports which are useful as complexing agents, catalysts, reagents, adsorbents, chromatographic supports and as biologically active supports for reaction with functional materials, one example of which is a protein, for example in protein synthesis. Whilst various polymer backbone species are disclosed for azlactone functionalisation in the formation of these polymeric supports, there is no disclosure or suggestion in the reference of the use of polymers which themselves may have a particular function which it may be desired to exploit.

EP-A-0435004 and EP-A-0437075 (both Dow Corning Corporation) describe, respectively, chlorobenzyl functionalised and acrylic-functionalised siloxanes for use in the permanent waving of hair. Such functionalised siloxanes are useful as replacements for oxidising agents which are used in conventional perming treatments to cross-link reduced sulphur-sulphur bonds in hair proteins. Both of these disclosures, however, fail to address the problem of temporary retention on the hair of cosmetic agents such as film-forming conditioning and bodying/setting materials, and relate only to the well-documented use in the literature of certain types of cross-linking agent for the specific use in the cross-linking of a reduced hair structure.

With the above criteria in mind, it was an object of the present invention to ameliorate at least some of the above mentioned problems and to devise a means for achieving improved levels of retention of cosmetic agents on treated substrate surfaces, such that a desired one or more cosmetic benefits wanted of a particular treatment can be achieved readily and with a significantly longer lasting effect than has hitherto been the case using conventional application and deposition technology.

SUMMARY OF THE INVENTION

What we have now surprisingly found is that one can achieve such long-term retention of cosmetic agents on substrates which are frequently subject to cosmetic treatment by use of particular molecular "handles" which serve to chemically bond the cosmetic agent to characteristic functional groups exposed at the surface of the substrate, whereby a stable, long-term union between substrate and cosmetic active is created which is substantially more resistant to the rigours of post application treatments which cosmetic agent-treated substrates frequently are required to withstand.

Accordingly, a first aspect the present invention provides a method of treating a substrate with a cosmetic agent to impart thereto one or more cosmetic benefits, comprising:

(a) providing the cosmetic agent as molecules thereof having chemically bonded thereto at least one azlactone substituent moiety for reaction with a nucleophilic reactive site on the substrate; and (b) applying the azlactone functionalised cosmetic agent to the substrate to effect reaction of the or each azlactone moiety with a or a respective nucleophilic reactive site on the substrate;

whereby the molecules of cosmetic agent are chemically bound to the substrate to impart the one or more cosmetic benefits thereto.

The method of this invention is applicable particularly to substrates which present at their surface at least one species of nucleophilic reactive site selected from nitrogen containing functional groups, for example primary or secondary amine groups, oxygen-containing functional groups, for example hydroxyl groups, and sulphur-containing functional groups, for example thiol groups. In preferred embodiments of the invention, the substrate is an organic material selected from proteinaceous substances such as keratin, as found in hair, skin, nails and certain other body parts, other naturally occurring protein-based materials, e.g., silk, or a saccharide derived substance such as cellulose or a cellulose derivative, e.g. a natural product such as cotton. Thus, the invention may be applicable to a wide variety of substrates which are conventionally subjected to various types of cosmetic treatment. Particularly preferred substrates for application of cosmetic agents in accordance with the invention are fibrous materials such as human or animal hair, wool, cotton, silk and various textiles and fabrics. Frequently, the substrate may be characterised by predominantly free amine groups at its surface, which provide particularly useful nucleophilic reactive sites for chemical bonding with the azlactone functionalised molecules of cosmetic agent according to the invention, particularly when the reaction is carried out in an aqueous environment. Hydroxyl groups at the substrate surface may become more important for reaction with the azlactone functionalised cosmetic agent under non-hydrolytic solvent conditions, e.g. in non-aqueous, non-alcoholic solvents.

The azlactone functionalised cosmetic agent according to the present invention provides active species which are both applicable to stabilised incorporation into cosmetic compositions of conventional types, e.g. aqueous-based solutions or emulsions, and are able to be readily deposited from such compositions by conventional deposition technology and treatment regimes, and may even to some extent overcome some of the limitations and dispense with some of the criticalities associated with known deposition technology and cosmetic product formulation requirements.

The cosmetic active moiety of the azlactone functionalised cosmetic agents used in accordance with the invention may be any cosmetic benefit substance which is able to be functionalised by chemical reaction with the one or more azlactone substituent moieties and which impart a desired one or more tactile, visual or other cosmetic benefits when applied to and reacted with the substrate in accordance with the invention. In most embodiments, the cosmetic agent is a polymeric material which relies to at least some extent for its cosmetic properties on its polymeric structure, which is therefore preferred so that even when functionalised with the one or more azlactone substituent moieties the material retains its normal cosmetic function. Polymeric cosmetic agents suitable as the cosmetic active moiety in the actives for use in the invention will frequently be film-forming polymers, which may preferably fall into the category of either a conditioning agent or a styling/bodying/setting agent. Examples of suitable materials for constituting the cosmetic active moiety of the functionalised cosmetic materials used in the present invention are given and described in further detail hereinbelow.

Methods for the preparation of azlactone functionalised cosmetic agents for use in the present invention are described hereinbelow, as are methods by which the functionalised materials may be incorporated for use in cosmetic compositions such as those comprising aqueous-based solutions as emulsions.

In a further aspect of the present invention, therefore, there is provided a cosmetic composition for treating a substrate to impart thereto one or more cosmetic benefits, the composition comprising dissolved or dispersed particles of a cosmetic agent of which molecules thereof have chemically bonded thereto at least one azlactone substituent moiety capable of reaction with a nucleophilic reactive site on the substrate.

In a further aspect of the invention, there is provided the use for treating a substrate to impart thereto one or more cosmetic benefits of a cosmetic agent the molecules of which have chemically bonded thereto at least one azlactone substituent moiety capable of reaction with a nucleophilic reactive site on the substrate.

In yet a further aspect of the present invention, there are provided the above defined azlactone functionalised cosmetic agents per se, namely azlactone functionalised cosmetic agents for providing one or more cosmetic benefits, wherein molecules of the cosmetic agent have chemically bonded thereto at least one azlactone substituent moiety.

Preferred embodiments of the present invention, and the various aspects and features thereof, will now be described in detail.

DETAILED DESCRIPTION OF THE INVENTION

Azlactone Functionalised Cosmetic Agent

The cosmetic agent which characterises the various aspects of the present invention comprises at least one azlactone functionally chemically bonded to a backbone, preferably a polymeric backbone, which delivers one or more desired characteristic cosmetic benefits when deposited on the substrate to be treated. By "azlactone" is meant the following group:

Formula A

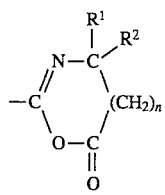

wherein $R^1$ and $R^2$ are the same or different and each is independently selected from H, and alkyl group having from 1 to 14 carbon atoms, particularly lower ($C_1$–$C_4$) alkyl e.g. methyl, a cycloalkyl group having from 3 to 14 carbon atoms, an aryl group having from 5 to 12 ring carbon atoms, an arenyl group having from 6 to 26 carbon atoms and from 0 to 3 S, N or O heteroatoms, or $R^1$ and $R^2$ taken together with the carbon atom to which they are joined can form a carbocylic ring containing 4 to 12 ring atoms, and n is an integer from 0 to about 12, e.g. from 0 to about 3.

When the azlactone functionalised cosmetic agent is applied to the preferred substrates in accordance with the invention, namely a substrate which comprises at its surface at least one nucleophilic group such as amine, hydroxyl or thiol, the azlactone group reacts with the nucleophile, resulting in a ring-opening reaction represented by the following equation:

Equation 1

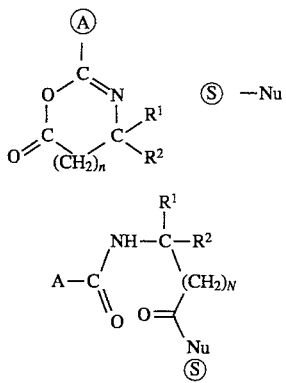

wherein A represents the cosmetic active moiety bonded to the azlactone group, S represents the substrate material and Nu represents a nucleophilic group at the substrate surface.

By this reaction the cosmetic active moiety carried by the azlactone functional group becomes chemically bonded to the substrate nucleophile, thereby creating a chemical link between the two. This chemisorption creates a bond between substrate and cosmetic active moiety, such that the cosmetic benefit or benefits provided by the cosmetic active are relatively long-term and may even be substantially permanent. This is very different from conventional cosmetic treatments of hair and other substrates, which rely on physisorbtion of the cosmetic active which is to impart its characteristic benefit(s). Because of the much weaker attractive and retentive forces between substrate and cosmetic agent in conventional systems, these known methods produce only short-lived and distinctly temporary cosmetic effects, which for film-forming cosmetic materials result in a perceivable benefit only for a period from one wash to the next, for example.

The cosmetic active moiety which is azlactone functionalised to produce the cosmetic agent material used in accordance with the invention is preferably a polymer and a wide range of polymers are suitable, depending upon the particular cosmetic benefit or benefits it is desired to obtain. Preferred polymers are those known polymeric materials for use in conventional cosmetic treatment products for the purpose of conditioning and/or for enhancing body, hold or stylability, particularly of hair and other fibrous materials. Examples of suitable substances which may form the cosmetic active backbones of the cosmetic agents of the present invention include the following:

(i) Silicone polymers, such as siloxane gums and resins, volatile or non-volatile silicone oils, amino- (or other) functional silicones, end-functionalised silicone polymers and other silicon-containing polymers known for use in cosmetic compositions in the art. Examples of suitable silicone polymers are widely published in the patent literature, including for example EP-A-0432951 (Unilever), EP-A-0530974 (Unilever), EP-A-0181773 (Procter and Gamble) and EP-A-0240350 (Procter and Gamble).

(ii) Hydrocarbon polymers, for example peralkyl(en)yl hydrocarbon materials such as polyisobutylene, as described for example in EP-A-0498119 (Unilever).

(iii) Perfluoro-aliphatic or -aromatic compounds, such as perfluoropolyether materials, as described for example in EP-A-0486135 (Unilever).

(iv) Chitosan and chitosan-based materials, such as salts of chitosan with various acids, preferably hydroxycarboxylic acids, polyaminoglucose-glycan polymer complexes, e.g. as described in EP-A-0403282.

(v) Cationic polymers, such as those disclosed in GB-A-2161172 (Beecham) GB-A-2122214 (Unilever) and GB-A-2050166 (L'Oreal).

(vi) In addition to those polymers mentioned in item (v) cationic conditioning polymers such as cationic derivatives of guar gum and cellulose ether derivatives, as mentioned for example in EP-A-0432951 and EP-A-0530974 mentioned above.

(vii) Other known film-forming polymers, such as polyvinylpyrrolidone/vinyl acetate copolymers.

(viii) Reactive derivatives of sunscreen materials, particularly UV absorbers, for example an allyl derivative of PARSOL MCX (ex Givaudan) ester, which is reactable with an activated azlactone moiety to give an azlactone-functionalised sunscreen for use in the invention.

(ix) Reactive dyes or colouring agents, e.g. conventional dyes or colours derivatised so as to be reactable with an activated azlactone moiety.

Disclosures of published references mentioned above are incorporated herein by reference.

The azlactone-functionalised cosmetic polymers may be prepared by conventional synthetic routes as are well known in the art from (a) at least one reactive species comprising a moiety providing the desired cosmetic benefit, and (b) at least one reactive species comprising the above-defined azlactone group. One particularly preferred family of reactive species (a) are those containing a vinyl unsaturation, for example a methacryloyl-substituted cosmetic polymer such as a siloxane, e.g. polydimethylsiloxane. Such monomers are particularly suitable for reaction with a vinyl unsaturated azlactone as species (b) of the reactive entities and are particularly suitable for radical addition polymerisation using conventional techniques. However, other polymerisation reactions, or other types of reaction, may be used, as are known to and will be well understood by persons skilled in the art and described for example in EP-A-0392735, the disclosure of which is incorporated herein by reference.

The reaction of the azlactone-containing species and the cosmetic active-containing species may take place between one or more of each species, to produce a product for use in the invention which comprises at least one moiety providing the cosmetic benefit(s) and at least one moiety constituting an azlactone "handle" for reaction with the substrate to be treated. The reaction may be a copolymerisation reaction involving both species (a) and (b) or may even be a terpolymerisation reaction with a third monomer which may be used to control certain properties of the resulting material, for example as regards its reactability with the nucleophilic substrate, its solubility or dispersibility in a given reaction medium or its action to produce a particular degree of or combination or one or more desired cosmetic benefits. Typical copolymerisation and terpolymerisation reaction protocols are well known in the art and specific examples are given in the examples hereinbelow. The reaction may alternatively be in the form of a grafting reaction, in which one or more (b) species are grafted onto a backbone of a polymer of species (a), or one or more (a) species are grafted onto a backbone of a polymer of species (b), to give the required azlactone functionalised cosmetic active product.

Starting materials for the above reactions or polymerisations may be either readily available commercially or may be prepared using known methods and protocols described in the technical and patent literature.

The azlactone functionalised cosmetic agent used in the invention may be monofunctionalised, i.e. the cosmetic active moiety carries a single azlactone group for reaction with the nucleophilic substrate, or it may be bis- or multifunctionalised, i.e. the cosmetic active moiety may carry two or more azlactone functionalities. The latter may be useful for example in achieving a greater degree of chemical bonding of the cosmetic agent to the substrate and may even be useful for generating chemical bonds between adjacent features of a single section of substrate or possibly even between different substrates, e.g. between fibres such as hair or textile fibres. The latter may for example be useful in achieving an enhanced degree of hair setting compared with prior art hair setting/styling methods.

Depending upon the degree of polymerisation and/or the number and nature of reactive species used, it is possible to produce an azlactone-functionalised cosmetic material having appropriate properties as regards stability in a composition into which it is to be incorporated, reactability with an intended nucleophilic substrate and also solubility. The latter property is important in determining the ease with which the material is incorporated into a desired cosmetic treatment composition and also possibly the means by which it is delivered to the site of reaction on the substrate.

In certain embodiments of the invention, preferred azlactone functionalised materials may be those which are water soluble or soluble in water/alcohol, e.g. ethanol, mixtures. This may enable compositions according to the present invention to be prepared as aqueous or aqueous/alcoholic solutions or emulsions, with or without additional ingredients such as those normally found in cosmetic products. The active materials used herein may be manufactured so as to have controlled selected solubility and/or dispersibility properties, thus making them tailor-made for stable incorporation into a particular product formulation and/or type from which they are intended to be delivered. Alternatively, the active materials for use in the invention may be soluble/ dispersible in organic solvents only, e.g. alcohols, hydrocarbons, etc. This may make them particularly suitable for formulation into mousse- or spray-type products.

Water-insoluble or water/alcohol insoluble azlactone functionalised materials may also be preferred in other embodiments of the invention.

In such embodiments, and possibly also others, suitable solvents for the azlactone functionalised cosmetic materials may include organic solvents, such as those well known in the art, e.g. volatile or non-volatile silicones, hydrocarbons, etc. Such solvents may be employed for example for the purpose of pre-dissolving a particular azlactone-functionalised material before incorporation into the final cosmetic composition, which may even be aqueous or non-aqueous based.

Generally, it is important that any additional ingredients present in the compositions of the invention do not affect the stability of the azlactone functionalised cosmetic agent or interfere with its ability to react with a nucleophilic group on the substrate to which the composition is applied. In this context, it has surprisingly been found that whilst it might have been expected that reaction of the functionalised cosmetic agent with a nucleophilic group of the substrate competes with hydrolysis of the azlactone moiety in an aqueous reaction medium, it has been found that the reaction of the azlactone with the substrate nucleophile is favoured over its hydrolysis. This means that it is all the more useful to be able to incorporate the active materials of the present invention in aqueous or aqueous-based products, which are by nature relatively cheap and easy to manufacture, store, transport and use.

Cosmetic Compositions Comprising the Azlactone Functionalised Cosmetic Agent

In this aspect of the present invention, a cosmetic composition comprises at least one of the above described azlactone-functionalised cosmetic agents, together with any additional ingredients which are normally to be found in cosmetic treatment compositions for use on hair, skin, or other substrates such as other fibres, textiles, fabrics or the like. One or more of the azlactone functionalised cosmetic agents may be used, the use of two or more being possible for example where a combination of cosmetic benefits is wanted, each derivable from a different cosmetic agent species.

Whilst aqueous or aqueous/alcoholic solution based compositions, or possibly organic solvent-based compositions, in which the one or more azlactone functionalised cosmetic agents are dissolved by solution are preferred, the compositions if desired or as appropriate may comprise stable emulsions of the one or more functionalised cosmetic agents which are designed to be water-insoluble. In both of these cases, conventional means for achieving successful deposition of the active(s) may need to be used, though, as will be described further below, this may not necessarily be the case so long as the active or actives are allowed to remain in contact with the substrate for a sufficient period of time for the characteristic chemical bonding to take place.

The one or more azlactone-functionalised cosmetic agents may be present in the compositions of the invention in comparable or smaller amounts than they would be used in conventional cosmetic treatment compositions relying for their efficacy on physisorption of the active on the substrate. Smaller amounts may be possible than has hitherto been the case because of the tendency for more of the material to be retained on the substrate by chemical reaction as opposed to mere physisorption as in the prior art.

Typically, the azlactone functionalised cosmetic agent is present in the compositions of the invention in an amount from about 0.00001 to 20% by weight of the composition. Suitable ranges of amounts will generally depend upon the cosmetic material in question: for example, azlactone functionalised silicone conditioning agents may be present from about 0.01 to 10% by weight of the composition, and other film-forming polymers such as cationic conditioning polymers or polyisobutylene may for example be present from about 0.01 to 10% by weight of the composition, perfluoropolyether materials may be present from about 0.000001 to 0.01% by weight of the composition, and other film forming polymers such as cationic conditioning polymers or polyisobutylene may for example be present from about 0.01 to 2% by weight of the composition.

Whether or not a composition of the invention is in the form of an emulsion, in which case an emulsifier is preferably included to stabilise the emulsified particles of the active, as is well known in the art, it may contain one or more surfactants in order to provide detergent action simultaneously with the imparting of the cosmetic benefit(s) characteristic of the cosmetic agent, and/or possibly to enhance the ease of reaction of the azlactone functional group with the nucleophilic group on the substrate.

Preferred surfactants, which may be used singularly or in combination, are selected from anionic, nonionic, amphoteric and zwitterionic surfactants, and mixtures thereof.

Suitable anionic surfactants are the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain an average of from 1 to 10 ethylene oxide or propylene oxide units per molecule, and preferably contain 2 to 3 ethylene oxide units per molecule on average.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$–$C_8$) primary or secondary linear or branched chain alcohols or phenols with alkylene oxides, usually ethylene oxide and generally having from 6 to 30 ethylene oxide groups.

Other suitable nonionics include mono- or di- alkyl alkanolamides. Examples include coco mono- or di-ethanolamide and coco mono-isopropanolamide.

Further suitable nonionic surfactants are the alkyl polyglycosides (APG's). Typically, the APG is one which comprises an alkyl group connected (optionally via a bridging group) to a block of one or more glycosyl groups. Preferred APG's are defined by the following formula:

RO—(G)

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues or mixtures of $C_5$ and $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

The surfactant(s) may be present in the cosmetic compositions of the invention in a total amount of from about 1 to about 40% by weight, preferably from about 2 to about 30% by weight.

If desired or as necessary, one or more additional cosmetic benefit agents may also be included in the compositions of the invention, for example to modify the overall cosmetic benefit or combination of benefits imparted to the substrate treated with the composition. Suitable additional cosmetic benefit agents include the following:

(i) conditioning agents, i.e., materials which impart one or more visual or tactile benefits such as softness, smoothness, shine, non-flyaway, anti-static, ease of dry and/or wet combing, e.g. cationic surfactants, cationic polymers, volatile and/or non-volatile silicones or derivatives thereof, quaternary ammonium salts having at least one long chain alkyl or alkenyl group, protein hydrolysates, quaternized protein hydrolysates, perfluoropolyether materials, fatty alcohols, and mixtures thereof;

(ii) styling/setting/bodying agents, i.e. materials which give enhanced body and feel to hair or other fibres or enable them to hold a given shape or style, e.g. various polymers, gums and resins, for example adhesive and/or resinous hydrocarbon materials such as per-alk(en)yl hydrocarbon materials, silicone/siloxane gums or resins, waxes, chitosan and derivatives, salts and complexes thereof, and mixtures thereof;

(iii) fibre straightening agents;

(iv) colourants and dyeing agents;

(v) antidandruff agents, e.g. zinc pyridinethione, octopirox (trade mark), climbazole;

(vi) sun-protective materials, e.g. sunscreens, especially UV absorbers;

(vii) hair growth promoters or regulators, e.g. diacylglycerols, glucarolactams, glucarolactones, Minoxidol (trade mark);

(viii) moisturisers e.g. 2-hydroxyalkanoic acids, acid soap complexes thereof, and other emollients, occlusives, humectants;

(ix) pearlescent and/or opacifying materials;

(x) oils, e.g. silicone oils, oleic acid, hydrocarbons, isopropyl myristate, oleyl alcohol, oleates, squalene, sunflower seed oil, rapeseed oil, other plant derived oils, mineral oil;

(xi) proteins, vitamins, nutrients, stimulants, antiradicals, astringents;

(xii) herb or other plant extracts, essential oils, etc.

(xiii) antimicrobial agents, e.g. antibacterial or anti-infestive agents;

(xiv) other adjunct materials commonly used in cosmetic compositions, e.g. buffering and/or pH adjusting agents, perfumes, colourings, preservatives, proteins, etc.

We have found that the pH of the compositions of the invention is frequently important in achieving optimised chemisorption of the functionalised cosmetic agent on the substrate. The most suitable pH for a given composition may depend principally on the type and structure of the functionalised active, for example whether it contains one or two azlactone moieties per cosmetic active unit or whether it is a copolymer or a terpolymer.

In a preferred embodiment of the composition of the invention which comprises as the functionalised cosmetic agent a copolymer of for example a silicone conditioning agent with a vinylazlactone compound, the preferred pH of the cosmetic composition is in the range of from about 8 to 12. On the other hand, when the functionalised cosmetic agent is a terpolymer based on monomer units of vinylazlactone, vinylpyrrolidine and the same silicone conditioning agent, the preferred pH may be in the range of from about 3 or 4 to about 6 or 7.

Whilst not intending to be limited by theory, it is believed that this difference in optimum pH may be because the hydrolytic stability of the azlactone rings of the terpolymer is markedly less at the higher pH than at the lower pH, in contrast to the copolymer in which the converse is true. The higher pH conditions may thus cause appreciable depression of the reactive azlactone ring content of the terpolymer faster than the reaction of the azlactone moiety of the polymer can take place with the substrate. This could result therefore in less polymer being covalently bound to the substrate at the higher pH than at the lower.

This observation is furthermore surprising in that we have found there not to be a corresponding significant difference between the amount of cosmetic agent bound to the substrate at different temperatures for both pH range conditions which have been tested. This could be due to the substrate becoming saturated with bound cosmetic polymer by reaction of all available nucleophilic sites occurring at both temperatures.

If desired or as necessary, the compositions of the invention may include a catalyst or promoter to initiate or catalyse the reaction of the azlactone group of the active with the nucleophile of the substrate.

The cosmetic compositions according to the invention may be provided in any suitable physical form, for example as low to moderate viscosity liquids, lotions, milks, mousses, sprays, gels and creams.

It is generally important that when a given substrate is treated with a composition of the invention, the physical environment in the composition permits contact of the azlactone-functionalised cosmetic agent with nucleophilic sites on the substrate. Thus, not only is it desirable that the physical structure of the composition allows maximum contact of the active agent with the surface of the substrate, for which reason liquid products are preferred, but it is also especially desirable that treatment regimes allow for a period of time during which the active molecules in the composition remain in contact with the substrate to allow them to react and become bonded thereto.

Accordingly, in preferred methods of the invention wherein the azlactone-functionalised cosmetic agent is applied to the substrate to impart thereto one or more cosmetic benefits, it is particularly preferable for the treatment to include a retention step during which the composition containing the active is left in contact with the substrate for a period of time sufficient for the azlactone rings to react with the nucleophilic site on the substrate surface.

The invention will now be further illustrated by way of the following non-limiting examples:

EXAMPLES

In the following examples, the following polymers were used:

Polymers I, II and III

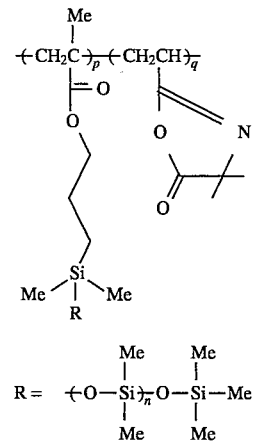

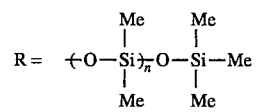

Polymer I: $p = 1, q = 2.9, n = 10$
Polymer II: $p = 1, q = 14.6, n = 60$
Polymer III: $p = 1, q = 29.3, n = 130$ Polymer IV

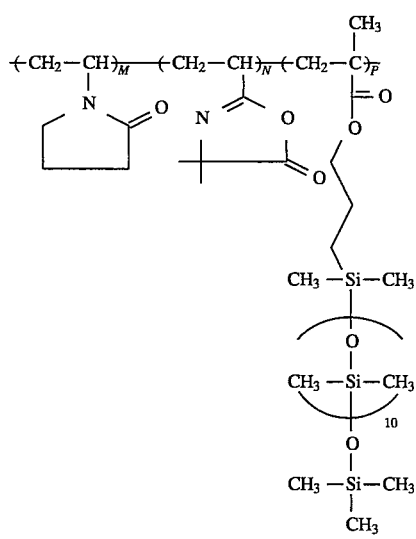

$m = 16$
$n = 1$
$p = 3$ (Note: the values of m, n, p and q represent the mole ratios of the monomers used in the reaction for the preparation of the polymers, and do not denote the polymer structure, i.e. whether random or block copolymers).

The above polymers were prepared by the following methods:

Polymers I, II and III

The reactants used were as follows:

(a) 2-Vinyl-4,4-dimethylazlactone (vinylazlactone) supplied by SNPE, Inc., Princeton, N.J.;

(b) Methacryloyl polydimethylsiloxane (PDMS) obtained from Chisso Corporation (Silicone Chemicals Group) Tokyo, Japan.

The silicone chain length of each of the PDMS starting materials used to prepare the three polymers was different in each case and was selected so as to give the required value of n in the above formulae of the three polymer products.

Vinylazlactone (3.5g), PDMS (8.5g), AIBN (240mg) and toluene (20ml) were charged into a polymerisation vessel fitted with a nitrogen inlet and a reflux condenser. The polymerisation was carried out at 70° C. for 48 hours. The resulting viscous solution was precipitated by dropwise addition into excess methanol with vigorous stirring. The polymer was vacuum dried at 50° C. for four hours and characterised by NMR and FT-IR spectroscopy.

Polymer IV

Vinylazlactone (0.5 g), PDMS (11.25 g), vinylpyrrolidone (5.11 g), AIBN (123 mg) and toluene (60 ml) were charged into a polymerisation vessel, and the polymerisation reaction was conducted as above and purified and characterised in a similar manner.

Example 1

Treatment of Hair with Azlactone Polymers I to III in Organic Solvent (Toluene)

Experimental

Bundles of hair fibres (switches) weighing 0.25 g 5.4 cm in length and tethered at one end were prepared from the root end of Yugoslavian red tie hair (ex Raoul, London). The switches were degreased by soaking in anionic surfactant (SLES 2EO, 2% aqueous solution) for 16 hours, rinsed in water and dried prior to use.

The switches were then soaked in 0.33% solutions of polymers I–III in toluene (15 ml per switch) in sealed vials at 50° C. for a period of 2 hours. Five replicate switches were used for each polymer treatment.

The switches were then blotted dry with tissue paper and stirred in fresh volumes of toluene (3×200 ml per batch of five) over a period of 24 hours. The switches were then stirred in propan-2-ol (3×200 ml per batch of five), again over a 24 hour period and allowed to air dry overnight.

The tether was removed from the ends of the switches and the free hair was mounted onto plastic support rings using double-sided sticky tape to fix the hair to the ring. The amount of silicone on the switches was then determined using a Phillips P1404 X-ray Fluorescence Spectrometer after placing the plastic support rings with mounted hair into the aluminium cup holders of the spectrometer.

The spectrometer was previously calibrated with hair containing known quantities of polydimethylsiloxane.

Results

The average amount of silicone on the hair for each set of five replicate switches for each polymer treatment is shown in the following table:

| Polymer Used | Amount of Silicone on Hair ppm |
| --- | --- |
| I | 580 (80)* |
| II | 660 (100) |
| III | 530 (20) |

*Figure in parentheses is the standard deviation.

Conclusion

The results indicate that the silicone containing azlactone copolymers I–III can react with hair to become covalently bound when applied in toluene solution under the conditions used above.

Example 2

Treatment of Hair with an Emulsified Toluene Solution of Polymer II

Experimental

Hair switches (0.25 g/5.4 cm) were prepared as in Example 1. These were treated with 0.55 g per switch of the following compositions.

| Emulsion A | | Emulsion B | |
| --- | --- | --- | --- |
| Ingredient | % w/w | Ingredient | % w/w |
| Polymer II | 9.1 | Polymer II | 9.1 |
| Toluene | 45.5 | Toluene | 45.5 |
| Water (to pH 7 with NaOH soln) | 45.4 | 0.1M Na$_2$CO$_3$ (aq (to pH 11 with NaOH soln) | 45.5 |

(Mixtures shaken to give viscous white emulsions)

Five replicate switches per treatment were used. The treatment involved spreading the emulsions evenly throughout the switches with an aluminium comb, sealing the switches in vials and storing in an oven at 50° C. for 1 hour.

The switches were then wiped free of the emulsion with Kleenex (trade mark) tissue and subjected to the following rigorous extraction procedure to remove non-covalently bound polymer from the hair:

(i) stirred in toluene (100 ml per switch) for 3 hours, blotted dry with Kleenex tissue and allowed to air dry at ambient temperature overnight.

(ii) Stirred in distilled water (2×200 ml per switch) for 3 hours and left to air dry.

(iii) stirred in toluene (100 ml per switch) for 3 hours and blotted dry.

(iv) stirred in propan-2-ol (3×100 ml per switch) for 3 hours and for a further 24 hours (100 ml per switch).

(v) stirred in 0.1M HCl (aq) for 1 hour and left to air dry.

(vi) stirred in toluene (2×100 ml switch) for 3 hours and allowed to air dry.

(vii) stirred in 0.1M Na$_2$CO$_3$(aq) (100 ml per switch) for 1 hour, then water (2×100 ml per switch) for 1 hour and allowed to air dry at ambient temperature.

The tethers were then removed from the switches, the free hair mounted on the plastic support rings and the silicone content of the hair determined as in Example 1.

Results and Discussion

The average amount of silicone on the hair for each set of five replicate switches for each emulsion treatment is shown in the following table:

| Treatment | Amount of Silicone on Hair (ppm) |
| --- | --- |
| Emulsion A | 2600 (500)* |
| Emulsion B | 4600 (680) |

*Figure in parentheses is the standard deviation.

These results indicate that polymer II can react with hair and become covalently bound even in the presence of water. (Water competes as a nucleophile for the azlactone ring of the polymer with the nucleophilic groups present in hair).

Whilst not wanting to be bound by theory, the finding that more polymer was bound to the hair at pH 11 than at pH 7 could be due to one or more of the following possible phenomena:

i) The reactivity of the important nucleophilic groups, e.g. amine groups of lysine residues, phenolic groups of tyrosine residues in the hair, is increased with increasing pH.

ii) The hair is more swollen at the higher pH enabling greater penetration of the polymer into the hair fibre and thus accessing more nucleophilic sites for reaction with the polymer.

iii) More nucleophilic groups are generated on the hair at the higher pH, perhaps as a result of hydrolysis of covalently bound fatty acids naturally present on the hair, for reaction with the polymer.

Conclusion

The results indicate that:

i) The silicone-containing azlactone copolymer II applied as an emulsified toluene solution can react with hair to become covalently bound even in the presence of water;

ii) More polymer is covalently bound to hair upon raising the pH.

Example 3

Test of Conditioning Effects of Azlactone Polymer III on Hair

Experimental and Results

Six hair switches (6.7 g/25.4 cm long) were prepared from Yugoslavian red tie hair and degreased by soaking in anionic surfactant solution (2% of SLES 2EO).

The switches were numbered 1 to 6. Switches 1 to 3 were assigned as control switches and were treated in the following manner:

Toluene (3.8 ml) was applied to each switch and evenly distributed along their lengths. This was immediately followed by the application of 0.1M $Na_2CO_3$ solution (3.2 ml to each switch) which was again evenly distributed. The switches were then sealed in glass tubes and stored in an oven at 50° C. for 1 hour.

Switches 4 to 6 were treated with 7 g per switch of the following composition:

| Ingredient | % w/w |
| --- | --- |
| Polymer III | 9.52 |
| Toluene | 45.24 |
| 0.1M $Na_2CO_3$ (aq) | 45.24 |

The treatment method was to evenly distribute this emulsion on the switches, seal each switch in a glass tube and heat them at 50° C. in an oven for 1 hour.

After the treatment all switches were removed from the glass tubes and subjected to the following extraction procedure sequence:

i) Wiped with tissue paper to remove the bulk of the liquid phase entrained between the fibres.

ii) Stirred in propan-2-ol (2×200 ml per switch) for 3 hours, wiped dry with tissue paper and allowed to air dry.

iii) Stirred in toluene (2×200 ml per switch) for 3 hours.

iv) Stirred in propan-2-ol (2×200 ml per switch) for 24 hours, blotted and allowed to air dry.

v) Stirred in 0.1M HCl(aq) (200 ml per switch) for 1 hour and blotted dry.

vi) Stirred in propan-2-ol (200 ml per switch) for 1 hour.

vii) Stirred in toluene (200 ml per switch) for 1 hour.

viii) stirred in propan-2-ol (200 ml per switch) for 5 minutes.

ix) Stirred in 0.1M $Na_2CO_3$(aq) (200 ml per switch) for 1 hour.

x) Stirred in water (200 ml per switch) for 1 hour.

The switches were then shampooed according to a standard protocol with a solution of anionic surfactant (16% SLES 2EO, 2×0.5 g per switch) and dried in a circulatory oven at 50° C. for 1 hour.

After removal from the oven the switches were allowed to cool at ambient temperature for 30 minutes before being subjected to the following sensory panel tests:

Smooth feel: the switches were assessed for smooth feel by a panel of twelve trained assessors using a paired comparison technique. Each panellist was presented with a total of six permutations of pairs of switches. Each pair comprised one switch selected from switches numbered 1 to 3 and the other from the switches numbered 4 to 6. Thus there was a total of 72 permutations of switches for the twelve panellists.

The result of the test was that the switches treated with the polymer III compositions were chosen 54 times out of the total of 72 assessments as having the superior smooth feel. This result is significant with >99% confidence.

Each of Combability: the switches were assessed for ease of combability by a panel of twelve trained assessors. Each panellist was again presented with six permutations of pairs of switches as described above.

The result of this test was that the switches treated with the polymer III composition were chosen 66 times out of the total of 72 assessments as having superior ease of combability. This result is significant with >99% confidence.

Conclusion

Treatment of hair with Polymer III applied as an emulsified toluene solution under the conditions used above gave a "permanent" conditioning effect to the hair in that the effect survived rigorous solvent extraction and shampooing.

The effect is ascribed to the polymer being covalently bound to the hair and thus being able to withstand the extraction procedure.

Example 4

Treatment of Hair with Water Dispersible Azlactone Polymer IV

Experimental

Hair switches (0.25 g, 5.4 cm long) were prepared from root end Yugoslavian red tie hair as described previously. The switches were treated with 0.5 g per switch of the following compositions (two sets of five replicates per composition):

| Dispersion A* | | Dispersion B | |
| --- | --- | --- | --- |
| Ingredient | % w/w | Ingredient | % w/w |
| Polymer IV | 5 | Polymer IV | 5 |
| Water | 95 | 0.1M NaCO$_3$ (aq) | 95 |
| (pH 3.7 Natural) | | (pH 11) | |

*Polymer IV gave a slightly hazy suspension when mixed with water with most of the solid appearing to have dissolved.

The treatment method was to evenly distribute the composition along each switch and seal them in vials. One set of five switches for each composition was then stored at ambient temperature for 1 hour and the other set for each composition was heated at 50° C. in an oven for 1 hour.

All the switches were then rinsed under running tap water at 50° C. with finger agitation for 2 minutes per switch. The switches were then stirred in SLES 2EO solution (2%, 4×500 ml per set of five switches) for 24 hours, rinsed under 50° C. tap water (1 minute per switch), shampooed with SLES 2EO (16%, 0.5 ml per switch for 2 minutes per switch), rinsed under 50° C. tap water (2 minutes per switch) and left to air dry overnight.

The silicone content of the switches was then determined using XRF spectroscopy as described previously.

Results and Discussion

The average amount of silicone on the hair for each set of five switches for treatment with Dispersions A and B at the two temperatures used is shown in the following table:

| Treatment | Temperature (°C.) | Amount of Silicone on Hair (ppm) |
| --- | --- | --- |
| Dispersion A | 22 | 4490(521) |
| " | 50 | 4449(761) |
| Dispersion B | 22 | 2766(575) |
| " | 50 | 2717(550) |

The results indicate that the water dispersible polymer IV reacted with hair to become covalently bound under all the conditions used. However, on this occasion it was found that less polymer was bound to the hair at the higher pH of 11 than at the lower pH of 3.7.

Whilst not wishing to be bound by theory, one reason for this finding could be that the hydrolyric stability of the azlactone rings of the polymer is markedly less at the higher pH than at the lower. The higher pH conditions may thus have caused appreciable depression of the azlactone ring content of the polymer faster than reaction of the polymer could take place with the hair. This could result in less polymer being covalently bound to the hair at the higher pH than at the lower.

Another surprising finding was that there was no significant difference between the amount of silicone bound at the two different temperatures for both pH conditions used. This could have been due to the hair becoming saturated with bound polymer by reaction of all available sites on the hair occurring at both temperatures.

Conclusion

The results indicate that the silicone-containing water soluble/dispersible polymer IV can react with hair to become covalently bound in the presence of water. However, the finding that less polymer was bound under alkaline than acid conditions suggests that polymer IV was less hydrolytically stable at the higher pH causing a depression of the azlactone ring content of the polymer resulting in less polymer being bound to the hair than at the lower pH.

Example 5

Test of Conditioning Effects on Azlactone Polymer IV on Hair

Experimental

Six hair switches (6.7 g/25.4 cm) that had a history of being repeatedly shampooed, combed and heated to dryness, i.e. damaged, were used in this experiment. The switches were numbered 1 to 6. Switches 1 to 3 were wetted with 7 g of distilled water and stored in sealed glass tubes at ambient temperature for 1 hour, (control switches). Switches 4 to 6 were treated with 7 g per switch of a 5% aqueous solution/suspension of polymer IV at its natural pH of 3.7. These switches were then also stored in glass tubes at ambient temperature for 1 hour.

All the switches were then rinsed under tap water at 50° C. for 2 minutes per switch with finger agitation. The switches were then dipped in SLES 2EO solution (16%), removed and shampooed for 2 min per switch, rinsed under 50° C. tap water for 2 min with finger agitation, soaked in SLES 2EO solution (5%) overnight (500 ml per switch), rinsed under 50° C. tap water for 2 mins then dried in a circulatory oven at 50° C. for 1 hour.

The switches were allowed to cool for 1 hour before being panel tested for smooth feel and ease of combability as described previously except that six trained panellists were used for assessing each attribute instead of twelve used previously.

Results

Smooth Feel: the result of this test was that the switches treated with polymer IV were chosen 35 times out of the total of 36 assessments as having the superior smooth feel. This result is significant with >99% confidence.

Ease of Combability: the result of this test was that the switches treated with polymer IV were chosen 36 times out of the total of 36 assessments as having the superior ease of combability. This result is significant with 100% confidence.

Conclusion

Treatment of hair with polymer IV in aqueous medium at ambient temperature gave a "permanent" conditioning effect to the hair which survived rigorous water and aqueous surfactant solution extraction.

The effect is ascribed to the polymer having become covalently bound to the hair and thus being able to withstand the extraction procedure.

We claim:

1. A method for treating hair to impart thereto a conditioning benefit, the method comprising applying to the hair an azlactone-functionalised copolymer consisting of vinyl azlactone and methacryloyl polydimethylsiloxane monomers; and allowing the copolymer to chemically bond through nucleophilic reaction of the azlactone onto the hair, the monomers of the copolymer being present in amounts sufficient to achieve both bonding to the hair and imparting conditioning properties.

2. A method for treating hair to impart thereto a conditioning benefit, the method comprising applying to the hair an azlactone-functionalized copolymer consisting of vinyl azlactone, vinyl pyrrolidone and methacryloyl polydimethylsiloxane monomers; and allowing the copolymer to chemically bond through nucleophilic reaction of the azlactone onto the hair, the monomers of the copolymer being present in amounts sufficient to achieve both bonding to the hair and imparting conditioning properties.

* * * * *